United States Patent
Baumann et al.

(10) Patent No.: US 6,596,906 B2
(45) Date of Patent: Jul. 22, 2003

(54) PROCESS FOR PREPARING FLUORINE-CONTAINING BENZALDEHYDES

(75) Inventors: Käthe Baumann, Wuppertal; Albrecht Marhold, Leverkusen, both of (DE)

(73) Assignee: Bayer Aktiengesellschaft, Leverkusan (DE)

(*) Notice: Subject to any disclaimer, the term of this patent is extended or adjusted under 35 U.S.C. 154(b) by 46 days.

(21) Appl. No.: 09/957,979

(22) Filed: Sep. 21, 2001

(65) Prior Publication Data

US 2002/0038055 A1 Mar. 28, 2002

(30) Foreign Application Priority Data

Sep. 25, 2000 (DE) .......................................... 100 47 293

(51) Int. Cl.$^7$ .............................................. C07C 45/63
(52) U.S. Cl. ........................ 568/437; 568/426; 568/435
(58) Field of Search ................................ 568/437, 426, 568/435

(56) References Cited

U.S. PATENT DOCUMENTS 4,420,433 A   12/1983   Braden et al. ........... 260/544 D

OTHER PUBLICATIONS

Detweiler et al, Journal of the American Chemical Society, 72, 2882–4 (1950).*
Chem. Ber. 129, (month unavailable) 1996, pp. 233–235, Jacek, Porwisiak and Manfred Schlosser, "1–Bromo–3,5–bis(trifluoromethyl)benzene: A Versatile Starting Material for Organometallic Synthesis".
Eur. J. Med. Chem.–Chimica Therapeutica, Sep.–Oct. 1979, 14, No. 5, pp. 411–414, John Ch. Eriks, Henderikus van der Goot and Wijbe Th. Nauta, "The rearrangement of some 2–phenyl–1,3–indandiones to (Z)–3–benzylidenephthalides".
J. Am. Chem. Soc., (month unavailable) 1985, 107, pp. 2442–2448, Christopher Blackburn, Ronald F. Childs, Dieter Cremer and Jürgen Gauss, Steromutation of Methoxycarbenium Ions. 2. Experimental Evidence for an Inversion Process.
Organic Reactions, vol. 4, (month unavailable) 1979, p. 362 and pp. 368–377, Erich Mosettig and Ralph Mozingo, "The Rosenmund Reduction of Acid Chlorides to Aldehydes".
J. Chem. Soc. Perkin Trans. 2, (month unavailable) 1987, pp. 639–649, Joyce C. Lockhart, Martin B. McDonnell, William Clegg and M.N. Stuart Hill, "Structure and Dynamics of Crowns containing the Phenyldinaphthylmethane Subunit (a Three–bladed Propeller): Observations of Correlated Rotation of the Propeller Blades and Certain Ether Segments".
Journal of Medicinal Chemistry (month unavailable) 1972, vol. 15, No. 7, pp. 775–780. Edward A. Nodiff, Andrew J. Saggiomo, Masafu Shinbo, Eugene H. Chen, Hirotaka Otomasu, Yasuaki Kondo, Toyohiko Kikuchi, Basant L. Verma, Shin Matsuura, Keiichi Tanabe, Mahesh P. Tyagi and Shiro Morosawa, "Antimalarial Phenanthrene Amino Alcohols. 2. Trifluoromethyl–Containing 9–Phenanthrenemethanols".
J. Med. Chem. 16, (month unavailable) 1973, pp. 1399–1401, Eugene L. Stroaryn, Effect of Trifluoromethoxy, Chlorodifluoromethoxy and Trifluoromethyl on the Antimalarial Activity of 5–Benzyl–and 5–Phenyl–2,4–diaminopyrimidines.
Burger; Hornbaker: "Some aromatic trifluoromethyl derivaives. The Rosenmund Reduction of trifluoromethylbenzoic acids" J. Org. Chem., Bd. 18, 1953, Seiten 192–194, XP001038078 *Seite 194, Zeile 25–38*.

* cited by examiner

Primary Examiner—Sreeni Padmanabhan
Assistant Examiner—Sikarl A. Witherspoon
(74) Attorney, Agent, or Firm—Godfried R. Akorli; Richard E.L. Henderson

(57) ABSTRACT

The invention relates to a particularly advantageous preparation of fluorine-containing benzaldehydes by reacting a corresponding aromatic acid chloride with hydrogen in the presence of a supported palladium catalyst and a catalyst moderator.

9 Claims, No Drawings

PROCESS FOR PREPARING FLUORINE-CONTAINING BENZALDEHYDES

BACKGROUND OF THE INVENTION

The present invention relates to a process for preparing fluorine-containing benzaldehydes by reduction of the corresponding aromatic acid chlorides.

Fluorinated benzaldehydes are important building blocks for active compounds in the pharmaceuticals sector. They can also be converted by reduction into the corresponding benzyl alcohols that likewise have a wide range of uses for active compounds in the pharmaceuticals sector.

Processes for preparing fluorine-containing benzaldehydes are known. Thus, fluorinated benzoyl chlorides are reduced to the corresponding benzaldehydes by a Rosenmund reaction (see Org. React. Vol. 4, 362) in sulfolane as solvent (EP-A 171 065). High yields are obtained in this way, but the use of a solvent means that the process has the disadvantage of a lower space-time yield and higher materials costs. Furthermore, especially for 3,5-bis(trifluoromethyl)benzoyl chloride, increased overhydrogenation of the benzoyl chloride to the corresponding benzene is observed.

Specifically for the preparation of 3,5-bis(trifluoromethyl)benzaldehyde, there are many known synthetic routes that are not all suitable for a preparation on a relatively large scale. Thus, the corresponding bromobenzene has been reacted with butyllithium and N,N-dimethylformamide (J. Med. Chem. 16, 1399 (1973) and Chem. Ber. 129, 233 (1996)). Due to the handling of pyrophoric organolithium compounds, this process has particularly high safety requirements.

The Grignard reaction of the corresponding bromobenzene with magnesium and triethyl orthoformate (Eur. J. Med. Chem. Chim. Ther. 14, 411 (1979)) has similarly high safety requirements for the handling of organomagnesium compounds.

The industrially difficult-to-obtain 3,5-bis(trifluoromethyl)benzyl alcohol has also been oxidized with pyridinium dichromate in moderate yield (J. Amer. Chem. Soc. 107, 2442 (1985)). This produces toxic chromium-containing waste that requires costly disposal.

A Stephen reduction of the corresponding nitrile using tin(II) chloride/hydrogen chloride gas (J. Chem. Soc. Perkin Trans. 2, 1987, 639) gives stoichiometric amounts of toxic tin salts as waste product.

Reduction of benzoyl chloride by means of tri-tert-butoxy-lithium-aluminum hydride in diglyme has also been described (J. Med. Chem. 15, 775 (1972)). However, aluminum hydrides can attack trifluoromethyl groups. A further disadvantage is the formation of stoichiometric amounts of aluminum salts that must be disposed of.

SUMMARY OF THE INVENTION

We have now found a process for preparing fluorine-containing benzaldehydes of the formula

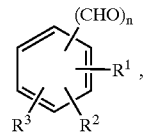

(I)

wherein
n represents 1 or 2, and
$R^1$, $R^2$, and $R^3$ each represent, independently of one another, hydrogen, fluorine, chlorine, bromine, $C_1$–$C_6$-alkyl, $C_1$–$C_6$-fluoroalkyl, $C_1$–$C_6$-fluoroalkoxy, or $C_1$–$C_6$-fluoroalkylthio, where at least one of the radicals $R^1$ to $R^3$ represents fluorine or a fluorine-containing radical and not more than two of the radicals $R^1$ to $R^3$ represents bromine, $C_1$–$C_6$-fluoroalkoxy, and/or $C_1$–$C_6$-fluoroalkylthio,
comprising reacting an aromatic acid chloride of the formula

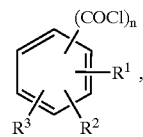

(II)

where $R^1$, $R^2$, $R^3$, and n are as defined for formula (I), with hydrogen in the presence of a supported palladium catalyst and a catalyst moderator.

If the radicals $R^1$ to $R^3$ are $C_1$–$C_6$-fluoroalkyl, $C_1$–$C_6$-fluoroalkoxy, or $C_1$–$C_6$-fluoroalkylthio, they can be monofluorinated, polyfluorinated, or perfluorinated $C_1$–$C_6$-alkylthio, $C_1$–$C_6$-alkoxythio, or $C_1$–$C_6$-fluoroalkylthio radicals.

The radicals $R^1$ to $R^3$ preferably each represent, independently of one another, H, F, Cl, Br, $CH_3$, $C_2H_5$, $CF_3$, $CF_2CH_3$, $C_2F_5$, $OCF_3$, or $SCF_3$, where at least one of the radicals $R^1$ to $R^4$ represents F, $CF_3$, $CF_2CH_3$, $C_2F_5$, $OCF_3$, or $SCF_3$ and not more than one of the radicals $R^1$ to $R^4$ represents bromine, $OCF_3$, or $SCF_3$.

If the radicals $R^1$ to $R^3$ are different from hydrogen and only one COCl group is present, they are preferably located in the 3, 4, and 5 position(s) of the benzene ring relative to the COCl group.

Particular preference is given to using mono-, di-, and trifluoro-benzoyl chlorides, mono- and bis-trifluoromethylbenzoyl chlorides, monotrifluoromethoxybenzoyl chlorides, and monochloro- and monobromotrifluoromethylbenzoyl chlorides in the process of the invention for preparing the corresponding fluorine-containing benzaldehydes.

The hydrogen can be employed, for example, at pressures in the range from 0.5 to 3 bar. It is preferably employed under atmospheric pressure. The hydrogen gas can be passed into the reaction mixture by means of, for example, a tube or a frit. The hydrogen gas can also be passed into the space above the mixture. The hydrogen gas is preferably passed into the reaction mixture.

Suitalble support materials for the supported palladium catalyst are, for example, carbon, aluminum oxides, silicates, silica, and barium sulfate. Preference is given to carbon and barium sulfate. The supported palladium catalysts can contain, for example, from 1 to 10% by weight of palladium. The weight ratio of supported palladium catalyst to the aromatic acid chloride used can be, for example, from 1:2 to 1:1000 (preferably from 1:5 to 1:500).

Suitable catalyst moderators are, for example, organic sulfur compounds. Preference is given to thiophenol, thioanisole, thiourea, sulfolane, and quinoline-sulfur complexes. Particular preference is given to quinoline-sulfur complexes as described, for example, in Org. Reactions, Vol. 4, 362, or can be obtained as described in the present Example 1 or by methods analogous thereto.

The weight ratio of catalyst moderator to supported palladium catalyst can be, for example, from 1:1 to 1:500 (preferably from 1:10 to 1:200).

The catalyst moderator can, for example, be initially charged together with the aromatic acid chloride and the catalyst. It is also possible for the supported palladium catalyst to be brought into contact with the catalyst moderator first, optionally in the presence of an auxiliary, and for the catalyst/moderator combination then to be used in the process of the invention.

After the reaction is complete, the catalyst can be separated off, e.g., by filtration, and reused in the next batch. This reuse can be repeated up to 5 or more times. Reused catalysts can generally be used without further addition of catalyst moderator.

The auxiliary can be, for example, a small amount of an aromatic hydrocarbon, a halogenated hydrocarbon, a halogenoaromatic, an aprotic amide, an acyclic or cyclic ether, or a sulfone. For the purposes of the present invention, the term "a small amount" is, for example, an amount of up to 2.5 ml per 100 g (preferably from 0.02 to 0.5 ml per 100 g) of aromatic acid chloride used.

The auxiliary can not only serve to improve contact between the supported palladium catalyst and the catalyst moderator, but also, for example, for slurrying a supported palladium catalyst already containing catalyst moderator before the addition of the aromatic acid chloride.

The reaction of the invention is carried out at temperatures at which the starting material is liquid, for example, at temperatures in the range from 20 to 200° C. If a starting material has a melting point above 2020 C., the melting point of the starting material is the lowest suitable reaction temperature. If a starting material boils at below 200° C. under atmospheric pressure, the reaction may be carried out under superatmospheric pressure so that the starting material remains in the liquid state. It is also advantageous to carry out the reaction of the invention at temperatures and pressures at which the respective product is liquid. In general, the reaction can be carried out at temperatures in the range from 70 to 130° C. at atmospheric pressure. Particularly preferred reaction temperatures are in the range from 80 to 120° C.

The reaction of the invention can be carried out, for example, by initially charging an aromatic acid chloride, a supported palladium catalyst containing a catalyst moderator, and optionally a small amount of auxiliary and setting the reaction conditions while introducing hydrogen. It is also possible for an aromatic acid chloride, a supported palladium catalyst, a catalyst moderator, and optionally a small amount of auxiliary to be initially charged and the reaction conditions to be set while introducing hydrogen.

The reaction is complete when the offgases from the reaction no longer have an acidic reaction. The workup of the reaction mixture, optionally after cooling and depressurization, can be carried out in various ways, for example, by distilling the fluorine-containing benzaldehyde prepared directly from the reaction mixture, optionally under reduced pressure.

It is also possible for the catalyst to be separated off first, e.g., by filtration, and the product then to be isolated from the filtrate by distillation, optionally under reduced pressure. In this case, a small amount of over-hydrogenated product (i.e., benzene derivative) and/or a small amount of any auxiliary used may be obtained as first fraction.

It is frequently also possible for the crude product obtained after separating off the catalyst to be used further as such, e.g., for preparing fluorinated benzyl alcohols by reduction.

The process of the invention makes it possible to prepare fluorinated benzaldehydes of the formula (I) in higher space-time yields, without solvent and with less overhydrogenation to the benzene stage than hitherto, with no toxic waste being obtained and no particular safety measures being necessary.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

60 g of freshly distilled quinoline and 10 g of sulfur were refluxed for 5 hours with stirring. The cooled mixture was diluted with 700 ml of toluene. This gave a solution of a quinoline-sulfur complex containing 100 mg of the complex per ml. 2.5 g of 5% palladium on barium sulfate, 0.25 ml of the solution of the complex and 250 g of 3,5-bis(trifluoromethyl)benzoyl chloride were placed in a reaction vessel at room temperature with exclusion of water. A gentle stream of hydrogen gas was then passed through the mixture at atmospheric pressure. The mixture was subsequently heated to 100–110° C. and hydrogen gas was continuously introduced at atmospheric pressure. After liberation of acidic offgases had ceased (12 hours), the mixture was cooled, the catalyst was separated off by filtration, and the filtrate was distilled at 27 mbar. A yield of 190.0 g of 3,5-bis(trifluoromethyl)benzaldehyde having a boiling point of 79° C. was obtained. This corresponds to a yield of 86% of theory. A small amount of a mixture of toluene and 3,5-bis(trifluoromethyl)benzene was obtained as first fraction during the distillation.

Example 2

1 g of 5% palladium on barium sulfate (recovered from Example 1) and 100 g of 4-trifluoromethylbenzoyl chloride were placed in a reaction vessel at room temperature with exclusion of water. A gentle stream of hydrogen gas was then introduced at atmospheric pressure. The mixture was subsequently heated to 100–110° C. and hydrogen gas was introduced continuously at atmospheric pressure. After liberation of acidic offgases had ceased (6.5 hours), the mixture was cooled to room temperature, the catalyst was removed by filtration, and the filtrate was distilled at 33 mbar. At a boiling point of 82–86° C., 4-trifluoromethylbenzaldehyde was obtained in a yield of 45.9 g. This corresponds to a yield of 54% of theory.

Example 3

0.5 g of 5% palladium on barium sulfate (recovered from Example 1) and 48 g of 3-bromo-4-trifluoromethoxybenzoyl chloride were placed in a reaction vessel at room temperature with exclusion of water. A gentle stream of hydrogen gas was then introduced at atmospheric pressure. The mixture was subsequently heated to 100–110° C. and hydrogen gas was introduced continuously at atmospheric pressure. After liberation of acidic offgases had ceased (11 hours), the mixture was cooled to room temperature, the catalyst was removed by filtration and the filtrate was distilled at 25 mbar.

At a boiling point of 112° C., 3-bromo-4-trifluoromethoxybenzaldehyde was obtained in a yield of 31.3 g. This corresponds to a yield of 74% of theory.

Example 4

0.5 g of 5% palladium on barium sulfate (recovered from Example 1) and 50 g of 3-fluorobenzoyl chloride were placed in a reaction vessel at room temperature with exclusion of water. A gentle stream of hydrogen gas was then introduced at atmospheric pressure. The mixture was subsequently heated to 80–90° C. and hydrogen gas was introduced continuously at atmospheric pressure. After liberation of acidic offgases had ceased (9.5 hours), the mixture was cooled to room temperature, the catalyst was removed by filtration and the filtrate was distilled at 28 mbar. At a boiling point of 73° C., 3-fluorobenzaldehyde was obtained in a yield of 23.0 g. This corresponds to a yield of 57% of theory.

Example 5 (not according to the invention)

37 g of 3,5-bis(trifluoromethyl)benzaldehyde and 4 g of Raney nickel together with 150 ml of toluene were placed in a reaction vessel at room temperature. The vessel was pressurized with 30 bar of hydrogen gas and the mixture was hydrogenated at 50° C. for 7.5 hours while stirring. The mixture was subsequently cooled to room temperature, depressurized and the catalyst was filtered off. The filtrate was evaporated and the crude product obtained in this way was distilled at 17 mbar. 3,5-bis(trifluoro-methyl)benzyl alcohol having a boiling point of 97° C. was obtained in a yield of 31.5 g and a purity of 97.7%. This corresponds to a yield of 82.5% of theory.

What is claimed is:

1. A process for preparing fluorine-containing benzaldehydes of the formula

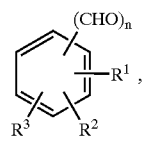

(I)

wherein n represents 1 or 2, and $R^1$, $R^2$, and $R^3$ each represent, independently of one another, hydrogen, fluorine, chlorine, bromine, $C_1$–$C_6$-alkyl, $C_1$–$C_6$-fluoroalkyl, $C_1$–$C_6$-fluoroalkoxy, or $C_1$–$C_6$-fluoroalkylthio, where at least one of the radicals $R^1$ to $R^3$ represents fluorine or a fluorine-containing radical and not more than two of the radicals $R^1$ to $R^3$ represents bromine, $C_1$–$C_6$-fluoroalkoxy, and/or $C_1$–$C_6$-fluoroalkylthio, comprising reacting an aromatic acid chloride of the formula

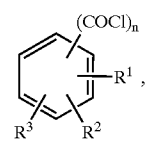

(II)

where $R^1$, $R^2$, $R^3$, and n are as defined for formula (I), with hydrogen in the presence of a supported palladium catalyst and a catalyst moderator.

2. A process according to claim 1 wherein the radicals $R^1$ to $R^3$ each represent, independently of one another, H, F, Cl, Br, $CH_3$, $C_2H_5$, $CF_3$, $CF_2CH_3$, $C_2F_5$, $OCF_3$, or $SCF_3$, where at least one of the radicals $R^1$ to $R^3$ represents F, $CF_3$, $CF_2CH_3$, $C_2F_5$, $OCF_3$, or $SCF_3$ and not more than one of the radicals $R^1$ to $R^3$ represents bromine.

3. A process according to claim 1 wherein the hydrogen is employed at a pressure in the range from 0.5 to 3 bar and a reaction temperature of from 20 to 200° C.

4. A process according to claim 1 wherein the supported palladium catalyst comprises from 1 to 10% by weight of palladium and carbon, aluminum oxides, silicates, silicas, or barium sulfate as a support material.

5. A process according to claim 1 wherein the weight ratio of the supported palladium catalyst to the aromatic acid chloride is from 1:2 to 1:1000.

6. A process according to claim 1 wherein the catalyst moderator comprises organic sulfur compounds.

7. A process according to claim 1 wherein the weight ratio of catalyst moderator to the supported palladium catalyst is from 1:1 to 1:500.

8. A process according to claim 1 wherein the catalyst is separated off after the reaction is complete and is reused without further addition of catalyst moderator.

9. A process according to claim 1 wherein the fluorine-containing benzaldehyde is isolated after the reaction is complete by distillation, optionally under reduced pressure and optionally after the catalyst has first been separated.

* * * * *